United States Patent
Gribble et al.

(10) Patent No.: US 7,919,500 B2
(45) Date of Patent: Apr. 5, 2011

(54) BIS-CARBAZOLE DNA INTERCALATING AGENTS FOR ANTITUMOR THERAPY

(75) Inventors: Gordon W. Gribble, Lebanon, NH (US); Dmitry A. Androsov, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 12/499,149

(22) Filed: Jul. 8, 2009

(65) Prior Publication Data

US 2010/0010033 A1    Jan. 14, 2010

Related U.S. Application Data

(60) Provisional application No. 61/078,859, filed on Jul. 8, 2008.

(51) Int. Cl.
*A61K 31/4353* (2006.01)
*A61K 31/437* (2006.01)
*A61K 31/403* (2006.01)
*C07D 209/82* (2006.01)
*C07D 209/88* (2006.01)
*C07D 471/02* (2006.01)
*C07D 471/04* (2006.01)

(52) U.S. Cl. .......... 514/285; 514/411; 546/70; 548/448; 548/440; 548/441; 548/444

(58) Field of Classification Search .......... 514/285, 514/411; 546/70; 548/448, 440, 441, 444
See application file for complete search history.

(56) References Cited

U.S. PATENT DOCUMENTS

| 2,503,889 A | 4/1950 | Silven et al. ............ 51/72 |
| 6,187,787 B1 | 2/2001 | Gribble et al. ............ 514/297 |
| 7,135,494 B2 * | 11/2006 | Munro et al. ............ 514/411 |

FOREIGN PATENT DOCUMENTS

JP    08044114 A  *  2/1996

OTHER PUBLICATIONS

Xu et al. Apoptosis 2008, 13, 413-422.*
Awada et al. Annals of Oncology 2002, 23, 1925-1934.*
Urban et al. J. Nat. Prod. 2002, 65, 1371-1373.*
Mayer et al. European Journal of Cancer 2004, 40, 2676-2704.*
Gourdie et al., "Synthesis and evaluation of DNA-targeted spatially separated bis(aniline mustards) as potential alkylating agents with enhanced DNA cross-linking capability", J. Med. Chem. 1991 34:240-248.
Jaycox et al., "Potential DNA bis-Intercalating agents:synthesis and antitumor activity of novel, conformationally restricted bis(9-aminoacridines)", J. Heterocyclic Chem. 1987 24:1405-1408.

* cited by examiner

*Primary Examiner* — Jason M Nolan
(74) *Attorney, Agent, or Firm* — Licata & Tyrrell P.C.

(57) ABSTRACT

The present invention is a DNA intercalating agent represented by the structure Y—Z—Y, wherein Y is an anti-tumor bis-carbazole and Z is a linear arrangement of multiple aromatic rings, containing at least two aromatic rings, or at least two alicyclic rings, wherein the rings are linked in a 1,4 or 1,3 manner. Methods of inhibiting cancer cells and treating subjects having cancer with these agents are also provided.

4 Claims, No Drawings

BIS-CARBAZOLE DNA INTERCALATING AGENTS FOR ANTITUMOR THERAPY

INTRODUCTION

This application claims benefit of priority to U.S. Provisional Patent Application Ser. No. 61/078,859, filed Jul. 8, 2008, and PCT/US2009/049560 filed Jul. 2, 2009, the contents of which are incorporated herein by reference in their entireties.

BACKGROUND OF THE INVENTION

Intercalation is one of several modes by which drugs interact with DNA wherein a planar portion of the drug is inserted in between adjacent stacked base pairs of a double stranded DNA. The intercalation process results in helix extension and unwinding of the DNA. Included within these drugs are anti-tumor agents, actinomycin D, adriamycin and daunomycin, as well as several drugs for treatment of parasitic disease including ethidium bromide, quinacrine, chloroquine and miracil D. U.S. Pat. No. 2,441,665 discloses a class of alkylene diamine derivatives which are valuable as antimalarial agents. U.S. Pat. No. 2,113,357 discloses basically substituted amino-acridine derivatives useful in treating blood parasites.

DNA intercalating ligands have been proposed for use in targeting alkylating agents to DNA by attachment of the intercalating ligand to the alkylating agent (Gourdie, et al. (1991) J. Med. Chem. 34:240-248). Since the biological properties of these DNA intercalating drugs are believed to result from their binding, efforts have focused on designing molecules that have a high affinity for DNA. Planar polycyclic aromatic molecules show a strong propensity to bind to DNA by intercalation (Jaycox, et al. (1987) J. Heterocyclic Chem. 24:1405-1408). To identify molecules with a greater affinity and selectivity for DNA, bifunctional intercalating agents in which two intercalating ligands are bridged by a central linking chain have been developed, wherein enhanced binding has been observed with molecules of this type (Canellakis, et al. (1976) Biochim. Biophys. Acta 418:277; Becker & Dervan (1979) J. Am. Chem. Soc. 101:3664; Wakelin, et al. (1986) Med. Res. Rev. 6:275). However, the chemical and physical nature of the linking chain has been found to play a role in the binding process.

For example, bis-intercalators bridged by flexible chains generally exhibit reduced affinities for DNA, in part because of self-stacking interactions which compete with the binding process (Barbet, et al. (1976) Biochemistry 15:2642; Capelle, et al. (1979) Biochemistry 18:3354). Further, bis-intercalation can introduce undesirable entropic effects when a flexible linker is forced into an extended chain conformation (Jaycox, et al. (1987) J. Heterocyclic Chem. 24:1405-1408). In addition, it is a concern that flexible bis-intercalators can creep in a stepwise fashion along the DNA macromolecule, thereby lowering ligand residence lifetimes at any one site (Denny, et al. (1985) J. Med. Chem. 28:1568). Such a process could have significant effects on efficacy of these intercalators as anticancer agents as residence lifetimes have been correlated with in vivo antitumor activity for a large number of DNA intercalators (Feigon, et al. (1984) J. Med. Chem. 27:450). Rigid tethers have been suggested as an (Jaycox, et al. (1987) J. Heterocyclic Chem. 24:1405-1408; U.S. Pat. No. 6,187,787).

SUMMARY OF THE INVENTION

The present invention relates to compounds of the structure Y—Z—Y, wherein Y is an anti-tumor bis-carbazole and Z is a linear arrangement of at least two aromatic rings or two acyclic rings arranged in a 1,4 or 1,3 configuration.

Methods of inhibiting cancer cell growth and treating cancer in a subject using a compound of the invention are also provided.

DETAILED DESCRIPTION OF THE INVENTION

The present invention relates to bis-carbazoles as DNA intercalating agents for use in the treatment of cancer. The bis-intercalators of the invention contain semi-rigid tethers that link two bis-carbazoles molecules, e.g., two pyridocarbazole molecules.

Compounds of the invention are represented by the structure Y—Z—Y, wherein Y is an anti-tumor bis-carbazole and Z is a linear arrangement of at least two aromatic rings or two acyclic rings arranged in a 1,4 or 1,3 configuration.

"Anti-tumor bis-carbazoles" are bis-carbazole compounds that exhibit anti-tumor activity in in vitro and/or in vivo assays. Anti-tumor bis-carbazoles are well-known and described in the art. For example, the plant alkaloid ellipticine is well-known for its gyrostatic activity (Dalton, et al. (1967) Aust. J. Chem. 20:2715; Svoboda, et al. (1968) J. Pharm. Sci. 57:1720). Similarly, U.S. Pat. No. 7,135,494 (incorporated herein by reference) discloses a series of caracole molecules exhibiting anti-tumor activity. Moreover, it has been shown that olivacine and 9-hydroxyellipticine are potent anti-temporal agents (Seth (1981) Brioche. Pharmacology. 30:2026), as is the olivacine derivative S 16020-2 (Goliad, et al. (1996) Cancer Chemotherapy. Pharmacology. 38:513-521). See also U.S. Pat. No. 4,851,417 and U.S. Patent Application No. 2007/0054905. The cytotoxicity of elliptic Ines, ellipitinium and 9-hydroxyl-derivatives such as 2-methyl-9-hydroxy-ellipticinium (NSC 264-137) has also been demonstrated (Paulette, et al. (1980) Recent Res. Cancer Res. 74:107-112). In particular embodiments, Y is selected from the group of anti-tumor bis-carbazoles including, but not limited to 1,4-dimethyl-carbazole (Pub hem Compound ID 96998) and pyridocarbazoles such as Ellipticine (Pub hem Compound ID 5288156), 9-Methoxyellipticine (Pub hem Compound ID 72512), 9-Hydroxyellipticin (Pub hem Compound ID 91643), Celiptium (Elliptinium, Pub hem Compound ID 42722), Bis-Elliptinium Bromide, 6-Methyl-Ellipticine (Pub hem Compound ID 97109), Ellipticine N-oxide (Pub hem Compound ID 315033), Ellipticine Derivative NSC359449 (Pub hem Compound ID 5458841), 6-(5-Hexen-1-eel)ellipticine (Pub hem Compound ID 294454), 9-Bromoellipticine (Pub hem Compound ID 97080), Olivacine (Pub hem Compound ID 5281407), Thioolivacine (Pub hem Compound ID 278065), S16020-2 (NSC-D-659687, (Pub hem Compound ID 177329), 2-Methyl-9-hydroxyellipticinium (Pub hem Compound ID 3034753), NSC311153 (Pub hem Compound ID 3086132), and NSC311152 (Pub hem Compound ID 3086131).

As indicated, Z is a linear arrangement of at least two aromatic rings or two acyclic rings arranged in a 1,4 or 1,3 configuration. In particular embodiments, Z is selected from a group of:

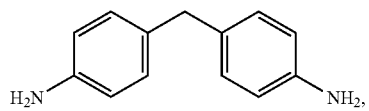

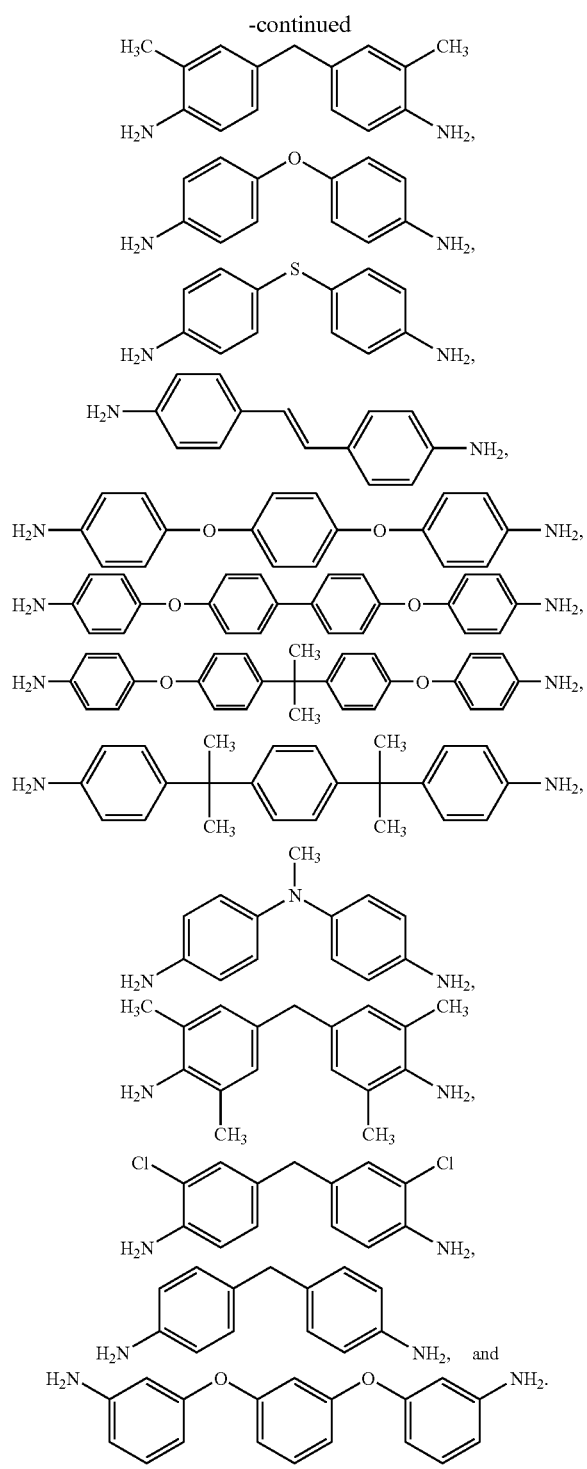

In particular embodiments, Z is attached via covalent bonds to NH or methyl groups of bis-carbazole compounds, e.g., using the methods disclosed herein. In addition, it is contemplated that Z can also be attached to any benzene ring of the bis-carbazole compounds of the invention.

U.S. Pat. Nos. 2,503,889 and 6,187,787 respectively disclose halogenated diacridine compounds and aminoacridine compounds with similar linking chains.

The compounds of the present invention are for use in binding to DNA in a tighter fashion than DNA intercalation agents currently in clinical use for the treatment of cancer. In addition, the compounds of the present invention are contemplated as being more effective inhibitors of cancer cells than the anti-tumor carbazoles disclosed in the prior art. Accordingly, compounds of the present invention will be useful in treating subjects suffering from cancer, such as leukemia, breast cancer, kidney cancer, lung cancer and the like. Indeed, it is contemplated that any cancer conventionally treated with an anti-tumor caracole will likewise be treated with a compound of the present invention.

The compounds disclosed herein can be synthesized according the procedures disclosed herein or any other suitable means of synthesis. Similarly, DNA binding and efficacy in the treatment of cancer can be demonstrated using conventional methods. For example, thermal denaturation studies can be performed on calf thymus DNA (see, e.g., Fiel, et al. (1979) *Nucleic Acids Res.* 6(9):3093-118; Nakaike, et al. (1992) *Jpn. J. Cancer Res.* 83(4):402-9; Fairley, et al. (1993) *J. Med. Chem.* 36(12):1746-53). In addition, the compounds can be analyzed for their ability to exhibit cytotoxicity in suitable cell line or animal models of cancer. For example, the murine leukemia cell line, L1210, is used in in vitro assays (Jaycox, et al. (1987) *J. Heterocyclic. Chem.* 24:1405-1408), as well as in in vivo assays, wherein CD2F1 mice receive L1210 leukemia cells by intraperitoneal injection (Edanami, et al. (1984) *Cancer Chemotherapy Pharmacology.* 13(1):22-6; Douzono, et al. (1995) *Jpn. J. Cancer Res.* 86(3):315-21). Similarly, the human mammary carcinoma MX-1 xenograft model is routinely used in the preclinical analysis of anti-tumor compounds in the treatment of breast cancer (Zhao, et al. (2008) *Bioconjug Chem.* 19(4):849-59; Wada, et al. (2007) *Anticancer Res.* 27:1431-5; Donawho, et al. (2007) *Clin Cancer Res.* 13:2728-37). In this model, NU/NU Swiss (nude) mice receive an intrarenal inoculation of MX-1 cells prior to or after treatment with the test compound. The human lung LX-1 xenograft model, wherein nude mice receive an intrarenal inoculation of LX-1 tumor cells, is also routinely used in the preclinical analysis of anti-tumor compounds (Masuda, et al. (2006) *J. Antibiot.* (Tokyo) 59(4):209-14). Similar models exist for the analysis of anti-tumor activity in prostate cancer (e.g., the TRAMP model, wherein transgenic mice develop spontaneous prostate cancer), skin cancer (e.g., the Mouse B16 Melanoma model), ovarian cancer (mouse ovarian carcinoma xenograft model; Davis, et al. (1993) *Cancer Research* 53:2087-2091) and kidney cancer (e.g., the murine renal cell carcinoma model (RENCA model)). Indeed, any suitable rodent or primate model can be used in the analysis of anti-tumor activity of the instant compounds. In each of these models, survival and/or tumor size is measured and the results are expressed as the measurement made in the treated group divided by the measurement made in the vehicle treated control group. Results of this analysis are expected to demonstrate that tumor size is decreased and or survival is increased in animals receiving treatment with a compound of the present invention.

Accordingly, the present invention also relates to methods of treating cancer, wherein an effective amount of a compound of the present invention is administered to the subject in need of treatment so that growth of the cancer cells is inhibited or decreased and the signs or symptoms of the cancer are ameliorated, decreased or reversed. In a particular embodiment, the compound is administered in a pharmaceutically acceptable carrier. Suitable pharmaceutically acceptable carriers are well-known in the art and are described for example in Remington: The Science and Practice of Pharmacy, Alfonso R. Gennaro, editor, 20th ed. Lippincott Williams & Wilkins: Philadelphia, Pa., 2000, a standard reference text in this field. Pharmaceutical carriers can be selected in accordance with the intended route of administration and the standard pharmaceutical practice. In a particular embodiment, an effective amount of compound of the present invention is administered to a subject intravenously or intratumorally and can be linked to a carrier which selectively targets tumor cells (e.g., an antibody). By "effective amount" it is meant a concentration or dose of a compound of the present invention which will inhibit cancer cell growth. Such dosages can be calculated routinely by those of skill in the art in accordance with in vitro and/or in vivo data from model systems and dosages used for other DNA intercalating agents in clinical use.

The invention is described in greater detail by the following non-limiting examples.

EXAMPLE 1

Synthesis of Bis-imines and Bis-amines

General Procedure for the Synthesis of Bis-imines (3). 1,4-Dimethyl-9H-caracole-3-carbaldehyde 1 (2 mmol), aryldiamine 2 (1 mmol), PTSA (catalytic amount—1 crystal) and toluene or benzene (100 ml) were charged into 250 ml round bottom flask. The mixture was refluxed with Dean-Stark distilling trap for 12 hours. After completion of the reaction, solvent was removed under reduced pressure, and solid residue was crystallized from $CH_2Cl_2$—MeOH to give the corresponding bis-imine 3 (Scheme 1).

SCHEME 1

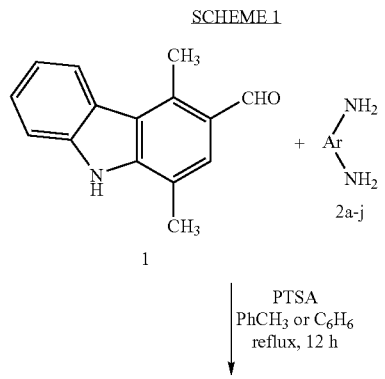

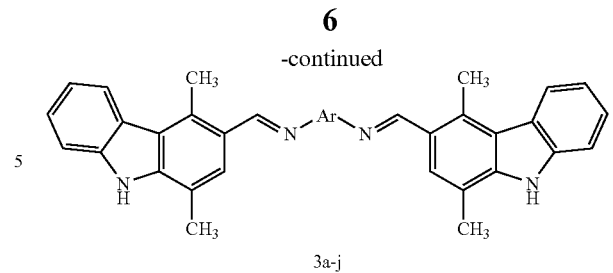

General Procedure for the Synthesis of Bis-amines (4). MeOH (100 ml) was added to the solution of bis-imine 3 (1 mmol) in DMF (10 ml) and the mixture was stirred and heated to reflux. $NaBH_4$ (5 mmol) was added portion wise (during a 5-minute period) and the mixture was refluxed for the additional 10 minutes. After cooling, MeOH was removed under reduced pressure and the residue was poured into water to give the precipitate of crude bis-amine 4 (Scheme 2). Bis-amine 4 was collected by suction and washed with water thoroughly. Recrystallization from $CH_2Cl_2$—MeOH afforded pure 4 as crystalline solid.

SCHEME 2

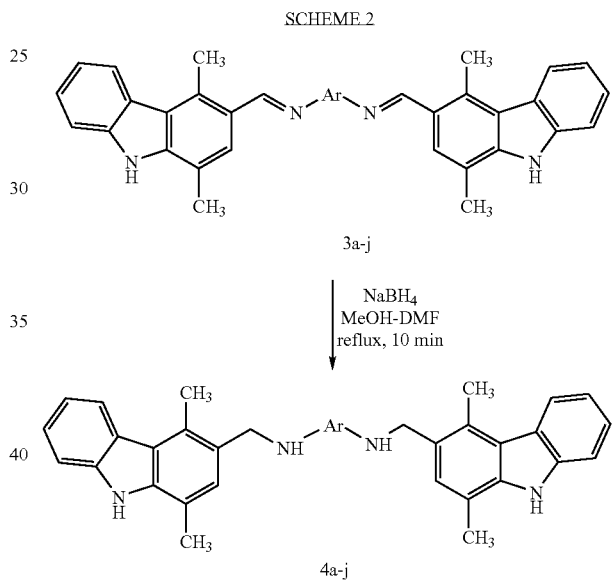

Yields of bis-carbazoles (3) and (4) are listed in Table 1.

TABLE 1

| Ar | Yield (%) | |
|---|---|---|
|  | Comp. 3 | Comp. 4 |
| 2a (H₂N-C₆H₄-CH₂-C₆H₄-NH₂) | 53 | 80 |
| 2b (H₂N-C₆H₃(CH₃)-CH₂-C₆H₃(CH₃)-NH₂) | 55 | 97 |

TABLE 1-continued
| Ar | Yield (%) | |
| --- | --- | --- |
| | Comp. 3 | Comp. 4 |
| 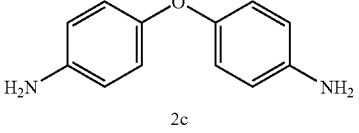<br>2c | 75 | 85 |
| 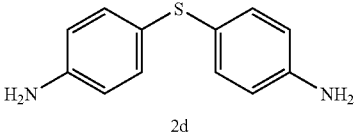<br>2d | 47 | 67 |
| 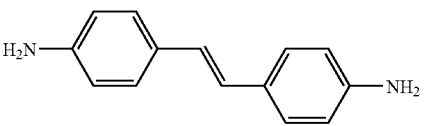<br>2e | 77 | 64 |
| 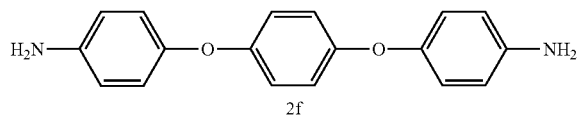<br>2f | 41 | 75 |
| 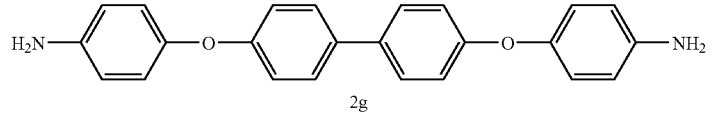<br>2g | 38 | 98 |
| 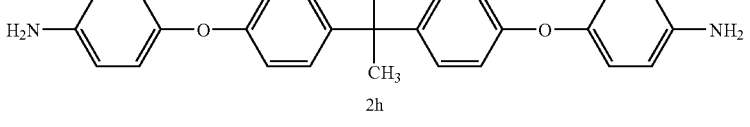<br>2h | 12 | 90 |
| 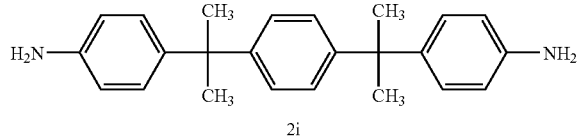<br>2i | 77 | 83 |
| 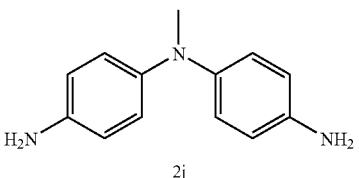<br>2j | — | 50 |

EXAMPLE 2

Synthesis of Bis-Acetylamine (5)

Bis-amine 4a (1 mmol) and Et$_3$N (2.5 mmol) were dissolved in CHCl$_3$ (50 ml) and the solution of acetyl chloride (2.2 mmol) in CHCl$_3$ (10 ml) was added dropwise at vigorous stirring. Subsequently, the mixture was stirred and refluxed for an additional 5 minutes. Addition of MeOH (50 ml) and displacement of CHCl$_3$ caused crystallization of the solid (Scheme 3). Bis-acetylamine 5 was filtered by suction, washed with MeOH, and recrystallized from CHCl$_3$—MeOH to give 5 (66% yield) as a white solid.

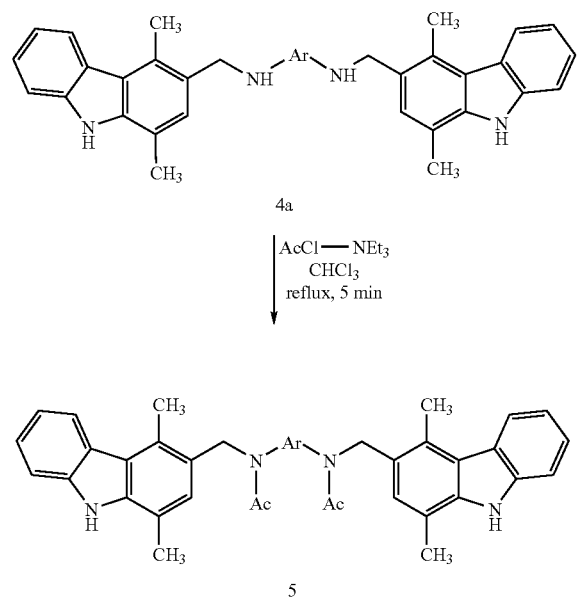

EXAMPLE 3

Synthesis of Bis-Elliptinium Bromides and Precursors

General Procedure for the Synthesis of Bis-Bromoacetyl Bromides (6). A solution of bromoacetyl bromide (2.2 mmol) in CHCl$_3$ (10 ml) was added dropwise to the solution of bis-amine 2 (1 mmol) and Et$_3$N (2.5 mmol) in CHCl$_3$ (30 ml) at 0° C. The resulting mixture was stirred for an additional 15 minutes at 0° C. Addition of MeOH (30 ml) and displacement of CHCl$_3$ at a low temperature (10-20° C., rotary evaporator) caused precipitation of 6 (Scheme 4). Bis-bromoacetyl bromide 6 was filtered by suction washed with small amount of MeOH, dried at room temperature, and used further without additional purification.

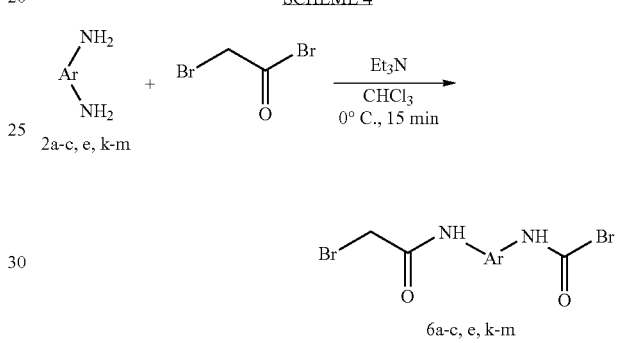

General Procedure for the Synthesis of Bis-elliptinium Bromides (8). A Solution of bis-bromoacetyl bromide 6 (1 mmol) and ellipticine (2 mmol) in DMSO (10 ml) was stirred and heated at 100° C. for 12 hours. After cooling, i-PrOH (30 ml) was added to precipitate solid 8 (Scheme 5). Bis-elliptinium bromide 8 was filtered by suction, washed with i-PrOH, and dried at 70° C.

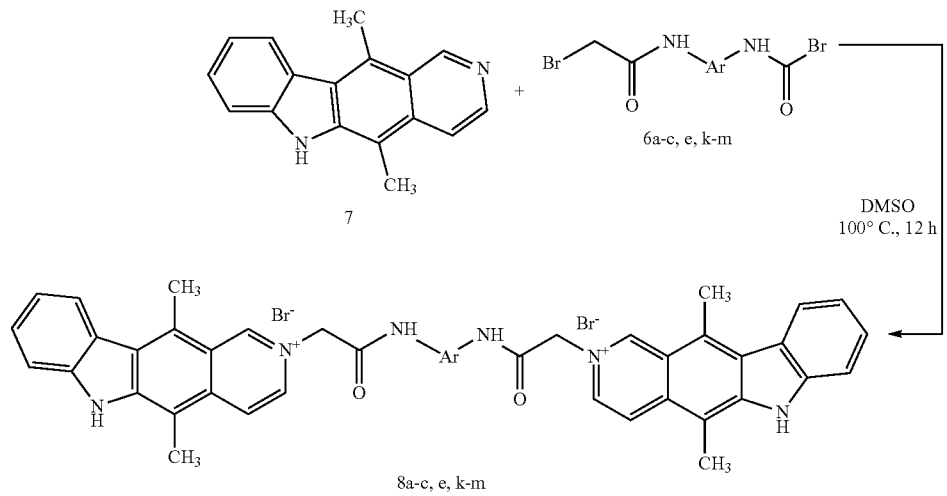

Yields of bis-elliptinium bromides (8) and the precursors (6) are listed in Table 2.

TABLE 2

| Ar | Yield (%) | |
|---|---|---|
| | Comp. 6 | Comp. 9 |
| 2a | 47 | 53 |
| 2b | 53 | 60 |
| 2c | 52 | 34 |
| 2e | 71 | 69 |
| 2k | 65 | 63 |
| 2l | 70 | 49 |
| 2m | 68 | 70 |

EXAMPLE 4

Cytotoxicity Evaluation in Leukemia Cells

L1210 murine leukemia cells are maintained as suspension cultures in McCoy's 5A medium supplemented with 10% horse serum, glutamine, penicillin, and streptomycin and grown in a humidified environment of 10% carbon dioxide and 90% air at 37° C. Compounds are dissolved in dimethyl sulfoxide (DMSO) and 40 µg of compound is added to 4 ml of L1210 cells ($10^5$ cells/tube) to attain final drug concentrations of 0.01, 0.1 and 10 µg/ml of culture. After 72 hours of continuous exposure to the drug, the cell concentration is determined by a Coulter counter (Model ZBF, Hialeah, FL). Growth inhibition is calculated for each drug concentration using the following formula:

% Growth Inhibition=$(1-A)\times100$, wherein A=[cell number treated/cell number in DMSO alone].

What is claimed is:

1. A compound consisting of the structure Y—NH—Z—NH—Y, Y=N—Z—N=Y, Y—N(Ac)—Z—N(Ac)—Y, or Y—C(O)—NH—Z—NH—C(O)—Y, wherein
   (a) Z is selected from a group of:

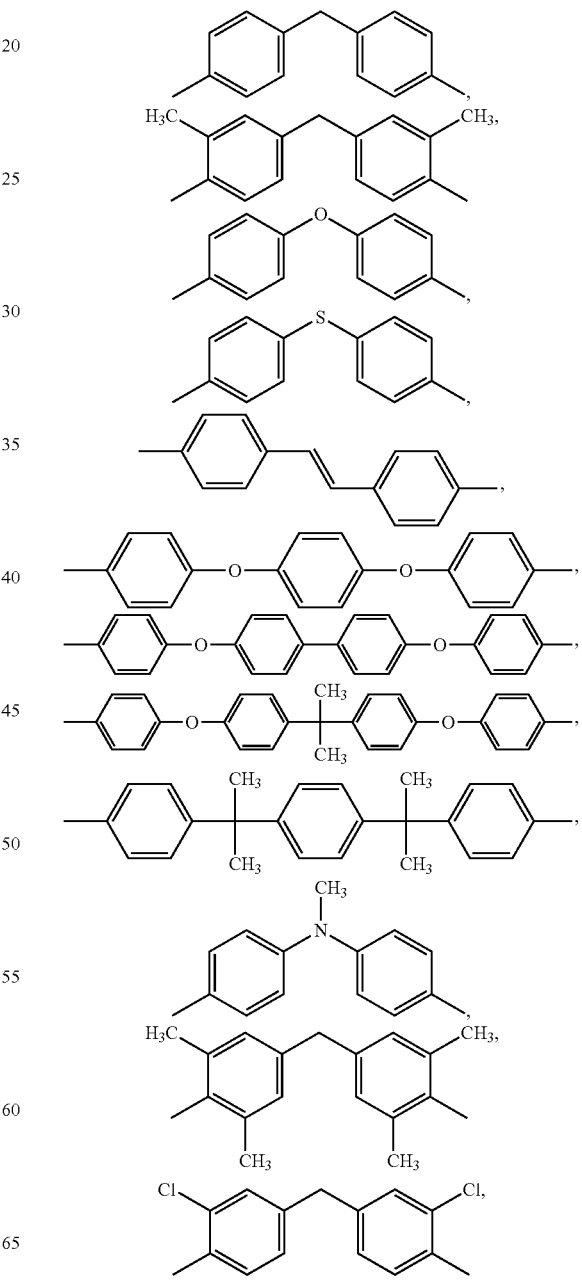

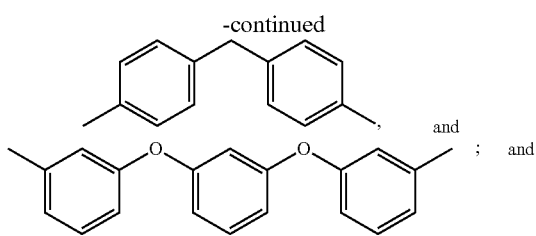

(b) Y is selected from the group of 1,4-dimethyl-carbazole, ellipticine, olivacine, and coproverdine, and derivatives thereof.

2. A pharmaceutical composition comprising a compound of claim 1 in a pharmaceutically acceptable carrier.

3. A method for inhibiting growth of a cancer cell selected from the group consisting of lung cancer, prostate cancer, colon cancer, leukemia, and melanoma, comprising contacting the cancer cell with an effective amount of a compound of claim 1 so that growth of the cancer cell is inhibited.

4. A method for treating a cancer selected from the group consisting of lung cancer, prostate cancer, colon cancer, leukemia, and melanoma, comprising administering to a subject in need of treatment an effective amount of a composition of claim 2 thereby treating the cancer in the subject.

* * * * *